(12) United States Patent
Frey, II

(10) Patent No.: US 6,180,603 B1
(45) Date of Patent: *Jan. 30, 2001

(54) METHOD FOR ADMINISTERING NEUROLOGIC AGENTS TO THE BRAIN

(75) Inventor: William H. Frey, II, White Bear Lake, MN (US)

(73) Assignee: Chiron Corporation, Emeryville, CA (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/780,335

(22) Filed: Jan. 8, 1997

Related U.S. Application Data

(63) Continuation of application No. 08/361,877, filed on Dec. 22, 1994, now Pat. No. 5,624,898.

(51) Int. Cl.[7] .......................... A61K 38/00; A61K 38/02; C07K 5/00; C07K 7/00

(52) U.S. Cl. ......................... 514/12; 530/300; 530/324; 530/402; 424/400; 424/430; 424/185.1

(58) Field of Search .......................... 514/12; 530/324, 530/300, 402; 424/400, 430, 185.1

(56) References Cited

U.S. PATENT DOCUMENTS

| | | |
|---|---|---|
| 4,464,368 | 8/1984 | Cox . |
| 4,479,932 | 10/1984 | Bodor . |
| 4,579,585 | 4/1986 | Fernö et al. . |
| 4,613,500 | 9/1986 | Suzuki et al. . |
| 4,639,437 | 1/1987 | della Valle et al. . |
| 4,746,508 | 5/1988 | Carey et al. . |
| 4,801,575 | 1/1989 | Pardridge . |
| 4,822,594 | 4/1989 | Gibby . |
| 4,895,452 | 1/1990 | Yiournas et al. . |
| 4,902,505 | 2/1990 | Pardridge et al. . |
| 4,921,705 | 5/1990 | Roberts et al. . |

FOREIGN PATENT DOCUMENTS

| | | |
|---|---|---|
| 0145209 | 6/1985 | (EP) . |
| 0333574 | 9/1989 | (EP) . |
| 0351808 | 1/1990 | (EP) . |
| 2260329 | 9/1975 | (FR) . |
| 1139444 | 2/1985 | (SU) . |
| WO 86/04233 | 7/1986 | (WO) . |
| WO 88/09171 | 12/1988 | (WO) . |
| WO 89/01343 | 2/1990 | (WO) . |

OTHER PUBLICATIONS

Altman, J., *Nature*, 337:688 (1989).

Ang et al., *Blood–cerebrospinal fluid barrier to arginine vasopressin, desmopressin and desglycinamide arginine–vasopressin in the dog*, J. Endocrin, 93, pp. 319–325 (1982).

Aoki et al., *Distribution and Removal of Human Serum Albumin—Technetium 99m Instilled Intranasally*, Br. J. Clin. Pharmac., 3, 869–878 (1976).

Boies et al., *Fundamentals of Otolaryngology*, W.B. Saunders Co., Philadelphia, pp. 184–185 (1989).

Broadwell, *Transcytosis of macromolecules through the blood–brain barrier: a cell biological perspective and critical appraisal*, Acta Neuropathol, 79, pp. 117–128 (1989).

Chien et al., Y.W., *In CRC Critical Reviews in Therapeutic Drug Carrier Systems*, 4:67–194 (1987).

Chien et al., *Nasal Systemic Drug Delivery*, Marcel Dekker, Inc., New York, pp. 18–19, 44–49, 56–59, 82–85, 292–293 (1989).

Doty, R.L., *Annals of N.Y. Acad. Sci.*, 561:76–86 (1989).

Editors, *Neurobiology of Aging*, 7:599 (1986).

Eisenbarth et al., *Monoclonal antibody to a plasma membrane antigen of neurons*, Proc. Natl. Acad. Sci. USA, 76, pp. 4913–4917 (1979).

Emory et al., *Ganglioside Monoclonal Antibody (A2B5) Neurofibrillary Tangles*, Fed. Proceedings, 45, p. 1728 (1986).

Emory et al. *Ganglioside Monoclonal Antibody (A2B5) Neurofibrillary Tangles*, Neurology, 37, pp. 768–772 (1987).

Eppstein et al., *Alternative Delivery Systems for Peptides and Proteins as Drugs*, CRC Critical Reviews in Therapeutic Drug Carrier Systems, 5, pp. 99–139 (1988).

Fabian et al., *Intraneuronal IgG in the central nervous system: Uptake by retrograde axonal transport*, Neurology, 37, pp. 1780–1784 (1987).

Ferreyra–Moyano, H., *Intern. J. Neuroscience*, 49:157–197 (1989).

Frey II et al., W.H., *Progress in Clinical Neuroscience*, 1:287–303 (1988).

Galanos et al., *Preparation and Properties of Antisera against the Lipid–A Component of Bacterial Lipopolysaccharides*, Eur. J. Biochem., 24, pp. 116–122 (1971).

Gopinath et al., *Target Site of Intranasally Sprayed Substances and Their Transport Across the Nasal Mucosa: A New Insight Into the Intranasal Route of Drug–Delivery*, Current Therapeutic Research, 23, pp. 596–607 (1978).

Gorio et al., *Neuroscience*, 8:417–429 (1983).

Graziadei et al., *Neurogenesis and neuron regeneration in the olfactory system of mammals. I. Morphological aspects of differentiation and structural organization of the olfactory sensory neurons*, J. Neurocytol, 8, pp. 1–18 (1979).

(List continued on next page.)

Primary Examiner—Avis M. Davenport
(74) Attorney, Agent, or Firm—W. Murray Spruill; Joseph H. Guth; Robert P. Blackburn

(57) ABSTRACT

Disclosed is a method for transporting neurologic therapeutic agents to the brain by means of the olfactory neural pathway and a pharmaceutical composition useful in the treatment of brain disorders.

41 Claims, No Drawings

OTHER PUBLICATIONS

Hammerschlag et al., *Axonal Transport and the Neuronal Cytoskeleton*, Basic Neurochemistry: Molecular, Cellular, and Medical Aspects, G.J. Siegel et al., eds., Raven Press Ltd., New York (4th ed.), pp. 457–478 (1989).

Hardy et al., *Intranasal Drug Delivery by Spray and Drops*, J. Pharm. Pharmacol., 37, 294–297 (1985).

Hefti et al., *Function of Neurotrophic Factors in the Adult and Aging Brian and Their Possible Use in the Treatment of Neurodegenerative Diseases*, Neurobiol. Aging, 10, pp. 515–533 (1989).

Kare et al., M.R., *Science*, 163:952–953 (1969).

Kasai et al., *The monoclonal antibody A2B5 is specific to ganglioside $G_{Q1c}$*. Brain Research, 277, pp. 155–158 (1983).

King, M., *The Atlanta Journal*, (Science/Medicine Section), Apr. 11, 1989.

Kristensson et al., *Acta neuropath*, (Berl.) 19:145–154 (1971).

Kumar et al, T.C., *Neuroendocrine Regulation of Fertility Int. Symp., Simla 1974*, Karger, Basel, (1976), pp. 314–322.

Kumar et al., T.C., *Current Science*, 43:435–439 (1974).

Kumar et al., *Pharmacokinetics of progesterone after its administration to ovariectomized rhesus monkeys by injection, infusion, or nasal spraying*, Proc. Natl. Acad. Sci. USA, 79, pp. 4185–4189 (1982).

Lee et al., *Intranasal Delivery of Proteins and Peptides*, BioPharm, pp. 30–37 (Apr. 1988).

Pearson et al., R.C.A., *Proc. Nat'l Acad. Sci.*, 82:4531–4534 (1985).

Phelps et al., C.H., *Neurobiology of Aging*, 10:205–207 (1989).

Pitha et al., *Drug Solubizers to Aid Pharmacologists: Amorphous Cyclodextrin Derivatives*, Life Sciences, 43, pp. 493–502 (1988).

Rapport et al., *Present Status of the Immunology of Gangliosides*, Advances in Experimental Medicine and Biology, R.W. Ledenn et al., eds., 174, pp. 15–25 (1984).

Represa et al., A., *Brain Res.*, 457:355–359 (1988).

Roberts, E., *Neurobiology of Aging*, 7:561–567 (1986).

Ryan, C., *Focus On*, University of Cincinnati Medical Center, 7:1–13 (1986).

Schofield, P.R., *TINS*, 11:471–472 (1988).

Seiler et al., M., *Brain Res.*, 300:33–39 (1984).

Shipley, M.T., *Brain Res.*, 15:129–142 (1985).

Snyder et al., *Molecular Mechanisms of Olfaction*, J. Biol. Chem., 263, pp. 13971–13974 (1988).

Stryer, *Biochemistry*, W.H. Freeman and Company, New York, pp. 288–291 (1988).

Talamo et al., B.R., *Nature*, 337:736–739 (1989).

Tiemeyer et al., M., *J. Biol. Chem.*, 264:1671–1681 (1989).

Williams et al., R., *Brian Research*, 463:21–27 (1988).

Young et al., *Production of Monoclonal Antibodies Specific for Two Distinct Steric Portions of the Glycolipid Ganglio–N Triosylceramide* (Asialo $GM_2$), J. Exp. Med., 150, pp. 1008–1019 (1979).

METHOD FOR ADMINISTERING NEUROLOGIC AGENTS TO THE BRAIN

This application is a continuation of Ser. No. 08/361,877 filed Dec. 22, 1994 and now U.S. Pat. No. 5,624,898.

FIELD OF THE INVENTION

The present invention is directed to a method for delivering neurologic agents to the brain by means of the olfactory neural pathway and a pharmaceutical composition useful in the treatment of brain disorders.

BACKGROUND OF THE INVENTION

Alzheimer's disease is an age-associated neurodegenerative disorder of the brain. The disorder is characterized histopathologically by the formation and accumulation of neurofibrillary tangles and neuritic plaques in the brain. In particular, pathological changes associated with the disease extensively affect neurons in the olfactory bulb and its connected brain structures. Degeneration with loss of neurons has been observed in the hippocampal formation, amygdaloid nuclei, nucleus basalis of Meynert, locus ceruleus, and the brainstem raphe nuclei, all of which project to the olfactory bulb. These degenerative changes result in the loss of memory and cognitive function. In addition, there is a major loss of cortical and hippocampal choline acetyltransferase activity and degeneration of basal forebrain cholinergic neurons. The loss of odor detection in Alzheimer's patents has been attributed to necrosis of olfactory epithelium, olfactory bulbs and tracts and the prepyriform cortex.

At present, there is no treatment for Alzheimer's disease which effectively prevents or retards the progressive neurodegeneration of the brain and the loss of smell and cognitive decline associated with the illness. Neurotrophic and neuritogenic factors, such as nerve growth factor (NGF) and gangliosides, have demonstrated therapeutic effects in animal models and cell cultures which indicate these substances may be of benefit to patients afflicted with Alzheimer's disease. See Frey, W. H., II and T. A. Ala, *Progress in Clinical Neuroscience* 1:287–303 (1988).

Neurotrophic and neuritogenic factors are agents that affect the survival and differentiation of neurons in the peripheral and central nervous systems. These growth promoting factors are signaling substances that are synthesized in tissues in response to neurons capable of responding to the factor. They bind to receptors on the surface of nerve cells to promote neuron survival and in some cases are incorporated into nerve cell membranes. Studies further indicate that nerve growth factor (NGF), a class of polypeptide signaling substances, may be capable of improving cholinergic functioning which would prevent injury-induced degeneration of basal forebrain cholinergic neurons and improve cognitive functioning. Nerve growth factor (NGF) is known to bind to receptors on axon terminals, and can be internalized and retrogradely transported to the cell body of neurons. See M. Seiler, *Brain Res.* 300:33–39 (1984). Other naturally-occurring nerve growth promoting factors include gangliosides, phosphatidylserine (PS), brain-derived neurotrophic factor, fibroblast growth factor, insulin, insulin-like growth factors, ciliary neurotrophic factor and glia-derived nexin.

Testing the effectiveness of potentially therapeutic agents against brain disease in animal toxicity studies and human trials has been hindered, however, by the inability of existing procedures to readily deliver adequate levels of the agent to affected areas of the brain over an extended period of time.

Some experimental therapeutic agents used in the treatment of Alzheimer's disease, such as GM-1 ganglioside, can be administered to the brain through the bloodstream because of their ability to traverse the blood-brain barrier. However, it is not clear that effective levels of the ganglioside reach the affected areas of the brain.

Other potentially therapeutic agents, such as nerve growth factor (NGF), are unable to cross the blood-brain barrier and must be administered to the brain by other means. One such method of delivery is by an intracerebroventricular pump. Use of such a pump, however, necessitates invasive surgery which can entail a variety of medically-related complications. Furthermore, administration of medication by pump does not facilitate selective delivery of medication solely to those areas of the brain affected by disease. Consequently, healthy areas of the brain may be adversely affected by the neurologic agent while some diseased areas may not receive a high enough level for adequate treatment or testing of a drug.

An effective method of therapeutic intervention is needed to prevent and effectively treat brain diseases such as Alzheimer's disease, Parkinson's disease, nerve damage from cerebrovascular disorders such as stroke, and ordinary aging. Testing the potential of various neurologic agents is an important aspect of developing treatments for neurodegenerative diseases. Since existing methods of testing possible therapeutic agents and treating brain disorders are of limited benefit, a goal of the present invention is to develop a procedure to effectively deliver neurologic agents to the brain. A particular goal of the invention is to develop a method of delivering neurologic substances to the brain to augment the level of activity against brain diseases by naturally-occurring substances. A further goal is to develop a means of selective delivery of a neurologic agent only to areas of the brain which are damaged by a brain disorder. Still another objective is to develop a composition that can cause absorption of the neurologic agent into olfactory neurons and along the olfactory neural pathway to damaged neurons in the brain. Another goal is to provide prophylactic treatment of neurodegenerative diseases and to treat and/or prevent associated loss of smell.

SUMMARY OF THE INVENTION

These and other goals are met by the present invention which is directed to a method to convey therapeutic substances to the brain for the treatment of neurologic or psychiatric disorders and a pharmaceutical composition capable of delivering a neurologic agent to the brain for use in such a method of treatment. More specifically, the method of medical treatment involves intranasal administration of a neurologic agent which may be absorbed into the olfactory system of the brain for the treatment of brain disorders such as Alzheimer's disease, Parkinson's disease, affective disorders such a depression and mania, nerve damage from cerebrovascular disorders such as stroke and the like.

According to the method of the invention, a neurologic substance is administered to the nasal cavity of a patient affected with Alzheimer's disease or other disease afflicting the brain. The neurologic factor may be applied alone or in combination with other substances. Particular formulations may include the neurologic substance in combination with a pharmaceutically-acceptable carrier and/or components that may facilitate the transfer of the neurologic agent through the nasal mucosa and/or along the olfactory neural pathway to damaged nerve cells of the brain.

The neurologic agent may be administered intranasally as a powder, spray, gel, ointment, infusion, injection, or drops.

The method of the invention may employ transneuronal anterograde and retrograde transport of the neurologic agent entering through the olfactory system of the brain. Once the agent is dispensed into the nasal cavity, the agent may transport through the nasal mucosa by means of the peripheral olfactory neurons into the olfactory bulb and interconnected areas of the brain such as the hippocampal formation, amygdaloid nuclei, nucleus basalis of Meynert, locus ceruleus, and the brainstem raphe nuclei. The agent alone may facilitate this movement into the brain. Alternatively, the carrier and/or other transfer-promoting factors may assist in the transport of the neurologic agent into and along the olfactory neural pathway.

Lipophilic substances in the form of micelles may be added to the pharmaceutical composition to enhance absorption of the neurologic agent across the olfactory epithelium. Among those substances that are preferred micellar additives are GM-1 gangliosides and phosphatidylserine (PS), which may be combined with the neurologic agent either alone or in combination.

The invention further provides a method for preventing neurodegenerative disorders. Intranasal administration of nerve growth promoting factors to peripheral nerve cells of the olfactory system, a purported entryway for causative agents of brain diseases, helps protect against disease in these nerve cells and regenerate injured nerve cells thereby forestalling the subsequent spread of disease to susceptible areas of the brain.

The invention is also directed to a pharmaceutical composition which may be used in the method of medical treatment and/or prophylaxis. The composition is comprised of a neurologic agent in combination with a pharmaceutical carrier and/or the foregoing optional additives which promote the transfer of the agent within the olfactory system.

The neurologic agent is the active ingredient of the composition. It is preferred that the neurologic agent promote nerve cell growth and survival or augment the activity of functioning cells. Among those agents that are preferred are neurotrophic and neuritogenic factors that are similar to naturally occurring nerve growth promoting substances. Among the preferred neurologic agents are gangliosides, phosphatylserine (PS), nerve growth factor (NGF), brain-derived neurotrophic factor, fibroblast growth factor, insulin, insulin-like growth factors, ciliary neurotrophic factor, glia-derived nexin, and cholinergic enhancing factors such as phosphoethanolamine and thyroid hormone T.3. GM-1 ganglioside and nerve growth factor (NGF) are particularly preferred. One or several neurologic substances may be combined together.

A preferred embodiment of the composition is the combination of an effective amount of nerve growth factor (NGF) protein with a pharmaceutically-acceptable liquid carrier containing an appropriate amount of micelles comprised of GM-1 ganglioside. GM-1 is thought to act synergistically with nerve growth factor (NGF) to protect neurons and promote nerve regeneration and repair. See Gorio et al., *Neuroscience* 8:417–429 (1983).

DETAILED DESCRIPTION OF THE INVENTION

The method of the present invention administers a neurologic agent to the nasal cavity of a human or other mammal for the testing of potential therapeutic agents against brain disease and for the treatment of brain disorders such as Alzheimer's disease, Parkinson's disease, affective disorders such as depression and mania, nerve damage from cerebrovascular disorders such as stroke or ordinary aging. In particular, the method delivers a neurologic agent to diseased areas of the brain by means of the olfactory neural pathway. The method may employ a pharmaceutical composition capable of transporting the neurologic agent to diseased neurons of the brain.

The method of the invention may achieve delivery of neurologic substances to afflicted areas of the brain through transneuronal retrograde and anterograde transport mechanisms. Delivery of neurologic agents to the brain by that transport system may be achieved in several ways. One technique comprises delivering the neurologic agent alone to the nasal cavity. In this instance, the chemical characteristics of the agent itself facilitate its transport to diseased neurons in the brain. Alternatively, the agent may be combined with other substances that assist in transporting the agent to sites of damaged neurons. It is preferred that auxiliary substances are capable of delivering the agent to peripheral sensory neurons and/or along neural pathways to dysfunctioning areas of the brain. It is further preferred that the peripheral nerve cells of the olfactory neural pathway be utilized in order to deliver the neurologic agent to damaged neurons in those regions of the brain that are connected to the olfactory bulb.

The neurologic agent that is administered by the method of the invention may be generally absorbed into the bloodstream and the neural pathway of the mammal. It is preferred that the agent exhibits minimal effects systemically. It is preferred that a large enough quantity of the agent be applied in non-toxic levels in order to provide an effective level of activity within the neural system against the brain disease. It is further preferred that the neurologic agent promote nerve cell growth and survival or augment the activity of functioning cells including enhancing the synthesis of neurotransmitter substances. Among those agents that are preferred are neurotrophic and neuritogenic factors that are similar to or the same as nerve growth promoting substances that are naturally occurring in the nervous system of a mammal. The agent may be administered to the nasal cavity alone or in combination with other neurologic agents. The agent may be combined with a carrier and/or other adjuvants to form a pharmaceutical composition. Among the preferred neurologic agents are gangliosides, nerve growth factor (NGF), phosphatidylserine (PS), brain-derived neurotrophic factor, fibroblast growth factor, insulin, insulin-like growth factors, ciliary neurotrophic factor, glia-derived nexin, and cholinergic enhancing factors such as phosphoethanolamine and thyroid hormone T.3. Among those agents that are particularly preferred are G-1 ganglioside and nerve growth factor (NGF).

The method of the invention delivers the neurologic agent to the nasal cavity of a mammal. It is preferred that the agent be delivered to the olfactory area in the upper third of the nasal cavity and particularly to the olfactory epithelium in order to promote transport of the agent into the peripheral olfactory neurons rather than the capillaries within the respiratory epithelium. The invention prefers the transport of neurologic agents to the brain by means of the nervous system instead of the circulatory system so that potentially therapeutic agents that are unable to cross the blood-brain barrier from the bloodstream into the brain may be delivered to damaged neurons in the brain.

It is preferred that the neurologic agent is capable of at least partially dissolving in the fluids that are secreted by the mucous membrane that surround the cilia of the olfactory receptor cells of the olfactory epithelium in order to be absorbed into the olfactory neurons. Alternatively, the invention may combine the agent with a carrier and/or other substances that foster dissolution of the agent within nasal secretions. Potential adjuvants include GM-1, phosphatidylserine (PS), and emulsifiers such as polysorbate 80.

To further facilitate the transport of the neurologic agent into the olfactory system, the method of the present invention may combine the agent with substances that enhance the absorption of the agent through the olfactory epithelium. It is preferred that the additives promote the absorption of the agent into the peripheral olfactory receptor cells. These peripheral neurons provide a direct connection between the brain and the outside environment due to their role in odor detection.

The olfactory receptor cells are bipolar neurons with swellings covered by hairlike cilia which project into the nasal cavity. At the other end, axons from these cells collect into aggregates and enter the cranial cavity at the roof of the nose. It is preferred that the neurologic agent is lipophilic in order to promote absorption into the olfactory neurons and through the olfactory epithelium. Among those neurologic agents that are lipophilic are gangliosides and phosphatidylserine (PS). Alternatively, the neurologic agent may be combined with a carrier and/or other substances that enhance the absorption of the agent into the olfactory neurons. Among the supplementary substances that are preferred are lipophilic substances such as gangliosides and phosphatidylserine (PS). Uptake of non-lipophilic neurologic agents such as nerve growth factor (NGF) may be enhanced by the combination with a lipophilic substance.

In one embodiment of the method of the invention, the neurologic agent may be combined with micelles comprised of lipophilic substances. Such micelles may modify the permeability of the nasal membrane and enhance absorption of the agent. Among the lipophilic micelles that are preferred are gangliosides, particularly GM-1 ganglioside, and phosphatidylserine (PS). The neurologic agent may be combined with one or several types of micelle substances.

Once the agent has crossed the nasal epithelium, the invention further provides for transport of the neurologic agent along the olfactory neural pathway. The agent itself may be capable of movement within the olfactory system. In particular, neurotrophic and neuritogenic substances have demonstrated ready incorporation into nerve cell membranes and an affinity for nerve cell receptor sites. Indications are that these substances are naturally synthesized in tissues in response to neural stimulation and that they subsequently bind to receptors on neurons where they act as nerve growth promoting factors.

Alternatively, the neurologic agent may be combined with substances that possess neurotrophic or neuritogenic properties which, in turn, may assist in transporting the agent to sites of nerve cell damage.

The invention also provides a means for the prevention of brain disorders particularly in cases where the causative factor enters the brain through olfactory neurons. It is preferred that prophylactic treatments be employed where evidence indicates neuronal degeneration in the olfactory neurons as in the case of Alzheimer's disease and other related brain disorders. Prophylactic treatment of brain disease may involve the direct or indirect application of neurologic therapeutic agents to the olfactory epithelium. Such agents may be absorbed into the peripheral olfactory nerve cells to protect those neurons from damage from neurotoxins and other insults and thereby prevent the spread of a disease-causing agent into other areas of the olfactory neural pathway and treat and/or prevent the loss of smell which may be associated with neurodegenerative diseases and aging. As in the foregoing methods of treatment, prophylactic therapies may apply the neurologic agent alone or in combination with a carrier, other neurologic agents, and/or other substances that may enhance the absorption of the agent into the olfactory neurons. Potential neurologic agents include gangliosides, nerve growth factor (NGF), phosphatidylserine (PS), brain-derived neurotrophic factor, fibroblast growth factor, insulin, insulin-like growth factors, ciliary neurotrophic factor, glia-derived nexin, and cholinergic enhancing factors such as phosphoethanolamine and thyroid hormone T.3. GM-1 ganglioside and nerve growth factor (NGF) are among those agents that are particularly preferred for prophylactic treatment of brain disorders.

To deliver the neurologic agent to the olfactory neurons, the agent alone or in combination with other substances as a pharmaceutical composition may be administered to the olfactory area located in the upper third of the nasal cavity. The composition may be dispensed intranasally as a powdered or liquid nasal spray, nose drops, a gel or ointment, through a tube or catheter, by syringe, by packtail, by pledget, or by submucosal infusion.

The optimal concentration of the active neurologic agent will necessarily depend upon the specific neurologic agent used, the characteristics of the patient and the nature of the disease or condition for which the treatment is to be used. The neurologic agent may be used alone or in combination with other substances as a pharmaceutical composition at such concentrations as 30 $\mu$M GM-1 ganglioside, 3 nM nerve growth factor (NGF), and 300 $\mu$M phosphatidylserine (PS). These concentrations are intended only as examples and do not exclude the use of other concentrations.

The invention is further directed to a pharmaceutical composition comprising an amount of a neurologic agent which is effective in treating or preventing brain disorders in a mammal, when administered thereto, in combination with a pharmaceutically-acceptable vehicle such as a liquid or powdered carrier and/or various optional adjuvants. The pharmaceutical composition is particularly useful for treating patients with Alzheimer's disease.

The neurologic therapeutic agent of the pharmaceutical composition may be any substance that promotes the survival of neurons and prevents the further loss of nerve cells. It is preferred that the agent has minimal systemic effects and augments the activity of naturally occurring nerve growth promoting factors. Preferably, the agent acts as a nerve growth promoting factor to prevent degeneration of neurons to induce regrowth of dendrite and axons and to augment the function of remaining neurons such as synthesizing neurotransmitter substances. Among the neurologic agents that are preferred are nerve growth factor (NGF), gangliosides, phosphatidylserine (PS), brain-derived neurotrophic factor, fibroblast growth factor, insulin, insulin-like growth factors, ciliary neurotrophic factor, glia-derived nexin, and cholinergic enhancing factors such as phosphoethanolamine and thyroid hormone T.3.

The carrier of the composition may be any material which is otherwise pharmaceutically-acceptable and compatible with the active ingredients of the composition. Where the carrier is a liquid, it is preferred that the carrier is hypotonic or isotonic with nasal fluids and within the range of pH 4.5–7.5. Where the carrier is in powdered form, it is preferred that the carrier is also within an acceptable non-toxic pH range.

Among the optional substances that may be combined with the neurologic agent in the pharmaceutical composition are lipophilic substances that may enhance absorption of the agent across the nasal membrane and delivery to the brain by means of the olfactory neural pathway. The neurologic agent may be mixed with a lipophilic adjuvant alone or in combination with a carrier. Among the preferred lipophilic substances are gangliosides and phosphatidylserine (PS). One or several lipophilic adjuvants may be combined with the agent. It is preferred that the lipophilic adjuvant be added as micelles.

The pharmaceutical composition may be formulated as a powder, granules, solution, ointment, cream, aerosol, powder, or drops. The solution may be sterile, isotonic or hypotonic, and otherwise suitable for administration by injection or other means. In addition to the neurologic agent, the solution may contain appropriate adjuvants, buffers, preservatives and salts. The powder or granular forms of the pharmaceutical composition may be combined with a solution and with diluting, dispersing and/or surface active agents. Solutions such as nose drops may contain antioxidants, buffers, and the like.

A preferred embodiment of the pharmaceutical composition of the invention is a micellar suspension of GM-1 ganglioside with an effective amount of nerve growth factor (NGF) combined with appropriate amounts of a stabilizer such as microcrystalline cellulose, a suspending agent such as carboxymethyl cellulose or hydroxypropyl methylcellulose, an emulsifier such as polysorbate 80, a preservative such as benzalkonium chloride, an antimicrobial such as phenylethyl alcohol, and a thickener such as dextrose.

The present invention for a method of administering neurologic agents useful in the treatment of brain disorders such as Alzheimer's disease presents several advantages over currently available methods.

The method of the present invention prefers the olfactory neural pathway rather than the bloodstream to deliver agents useful for the treatment of brain disorders such as Alzheimer's disease directly to the brain. Use of the olfactory system to transport a neurologic agent to the brain obviates the blood-brain barrier so that medications like nerve growth factor (NGF), a protein that cannot normally cross that barrier, can be delivered directly to the brain. Although the agent that is administered may be absorbed into the bloodstream as well as the olfactory neural pathway, the agent provides minimal effects systemically. In addition, the invention provides for delivery of a more concentrated level of the agent to neural cells since the agent does not become diluted in fluids present in the bloodstream. As such, the invention provides an improved method of testing potential therapeutic agents against brain disease and of treating neurodegenerative disorders.

The method provides an advantage by virtue of the intranasal administration of the medication. The olfactory system provides a direct connection between the outside environment and the brain thus providing quick and ready delivery of neurologic agents for treatment of neurologic disorders. Moreover, the means of applying a pharmaceutical composition intranasally can be in a variety of forms such as a powder, spray or nose drops which obviates intravenous or intramuscular injections and simplifies the administration of therapeutic medications. As such, the method of the present invention is an improvement over present methods of direct administration of neurologic therapeutic agents, such as the intracerebroventricular pump.

The application of a neurologic therapeutic agent to the nasal epithelium also helps prevent the spread of certain brain disorders by directly treating peripheral olfactory neurons that are injured by neurotoxins and other insults. Prophylactic treatment of these outlying nerve cells helps preclude the entrance of disease-causing agents into the brain. This method of treatment is particularly beneficial in cases of Alzheimer's disease where an environmental factor is suspected of being one of the causative agents of the disease. Application of a neurologic therapeutic agent to the olfactory sensory neurons also in part treats and/or prevents the loss of smell which may be associated with neurodegenerative diseases and ordinary aging.

Another advantage of the invention is that it provides delivery of neurologic agents solely to those areas of the brain affected by disease while avoiding unwanted treatment of brain regions which are free of the disease. The method of the invention employs a neurologic agent or other substance that has an affinity for neuron receptor sites in order to facilitate delivery of the agent directly to the brain through the olfactory epithelium.

The invention will be described with reference to various specific and preferred embodiments and techniques. However, it should be understood that many variations and modifications may be made while remaining within the spirit and scope of the invention.

EXAMPLE 1

Formulations of Pharmaceutical Compositions

Active Ingredients

Group 1. 30 $\mu$M GM-1 ganglioside (GM-1)

Group 2. 3 nM nerve growth factor (NGF)

Group 3. 300 $\mu$M phosphatidylserine (PS)

Group 4. 30 $\mu$M GM-1

3 nM NGF

Group 5. 30 $\mu$M GM-1

300 $\mu$M PS

Group 6. 3 nM NGF

300 $\mu$M PS

Group 7. 30 $\mu$M GM-1

3 nM NGF

300 $\mu$M PS

To formulate an aqueous preparation of the pharmaceutical composition, one or more of the following substances and/or carriers may be combined with any one of the aforementioned groups of active ingredients: microcrystalline cellulose, carboxymethyl cellulose, hydroxypropyl methylcellulose, polysorbate 80, benzalkonium chloride, phenylethyl alcohol, and dextrose. The preparation is to be maintained at a pH between 4.5–7.5. The concentration of active ingredients may follow the guidelines set forth above, but does not exclude the use of other concentrations or active ingredients.

Alternatively, any one group of the aforementioned active ingredients may be combined with propellants such as trichloromonofluoromethane or dichlorodifluoromethane, and delivered by an aerosol spray or similar application means as a non-aqueous preparation. Oleic acid may be added to the mixture as a lubricant.

EXAMPLE 2

Formulating Micelles

The compositions of Example 1 may further contain micelles consisting of GM-1 ganglioside and/or phosphatidylserine (PS). To formulate micelles, the lipid may be exposed to sonication in the aqueous solution of the pharmaceutical composition.

What is claimed is:

1. A method for transporting a neurologic agent to a brain of a mammal, comprising:

applying a pharmaceutical composition comprising the neurologic agent to an upper third of a nasal cavity of the mammal, wherein the neurologic agent is absorbed through a nasal mucosa and transported to the brain of the mammal.

2. The method of claim 1, comprising applying the pharmaceutical composition to an olfactory area in the upper third of the nasal cavity.

3. The method of claim 1, comprising applying the pharmaceutical composition to a roof of a nose.

4. The method of claim 1, comprising applying the pharmaceutical composition by employing a tube, a catheter, a syringe, a packtail, a pledget, a submucosal infusion, or a combination thereof.

5. The method of claim 1, wherein the pharmaceutical composition comprises a liquid, a powder, a spray, a nose drop, a gel, an ointment, an infusion, or combination thereof.

6. The method of claim 1, wherein the pharmaceutical composition comprises a pharmaceutically-acceptable carrier, a lipophilic micelle, a liposome, or a combination thereof.

7. The method of claim 6, wherein the lipophilic micelle or liposome comprises a ganglioside, a phosphatidylcholine, a phosphatidylserine, or a combination thereof.

8. The method of claim 1, wherein the pharmaceutical composition comprises a substance having an affinity for a receptor site on a neuron.

9. The method of claim 1, wherein the neurologic agent comprises fibroblast growth factor.

10. The method of claim 1, wherein the neurologic agent comprises basic fibroblast growth factor.

11. The method of claim 1, wherein the neurologic agent comprises insulin-like growth factor.

12. The method of claim 11, wherein the neurologic agent comprises insulin-like growth factor-1.

13. The method of claim 1, wherein the neurologic agent comprises insulin.

14. The method of claim 1, wherein the neurologic agent is transported to the brain by way of a nervous system instead of through a circulatory system.

15. The method of claim 1, wherein the neurologic agent is transported to the brain by way of an olfactory neural pathway.

16. The method of claim 15, wherein the neurologic agent is absorbed into an olfactory system of the brain.

17. The method of claim 15, wherein the neurologic agent is transported along a peripheral olfactory nerve into an olfactory bulb.

18. The method of claim 1, wherein the neurologic agent is transported to a hippocampal formation, an amygdaloid nuclei, a nucleus basalis of Meynert, a locus ceruleus, a brainstem raphe nuclei, or a combination thereof.

19. The method of claim 1, wherein the neurologic agent is transported to a brain stem, a cortical structure, a subcortical structure, or any combination thereof.

20. A method for administering a neurologic agent to a brain of a mammal, comprising:

applying a pharmaceutical composition comprising an effective amount of the neurologic agent to a nasal cavity of the mammal, wherein the neurologic agent is absorbed through a nasal mucosa and transported to the brain of the mammal along a neural pathway and in an amount effective for promoting growth of a brain cell, promoting survival of a brain cell, augmenting activity of a brain cell, providing a protective effect on a brain cell, or a combination thereof.

21. The method of claim 20, wherein the neurologic agent is transported to the brain by way of the neural pathway instead of through a circulatory system.

22. The method of claim 20, wherein the neurologic agent is transported to the brain by way of an olfactory neural pathway.

23. The method of claim 22, wherein the neurologic agent is absorbed into an olfactory system of the brain.

24. The method of claim 22, wherein the neurologic agent is transported through a peripheral olfactory nerve into an olfactory bulb.

25. The method of claim 20, wherein the neurologic agent is transported to the brain of the mammal in an amount effective for treating a neurological condition, a brain disorder, a psychiatric disorder, or a combination thereof.

26. The method of claim 25, wherein treating comprises treating or preventing brain disease or damage or inhibiting degeneration of nerve cells in the brain.

27. The method of claim 25, wherein treating comprises providing a protective effect on brain cells against or treating stroke.

28. The method of claim 25, wherein the condition or disorder comprises a neurodegenerative disorder, an affective disorder, nerve damage from a cerebrovascular disorder, or a combination thereof.

29. The method of claim 28, wherein the affective disorder comprises depression or mania.

30. The method of claim 28, wherein the neurodegenerative disorder is Parkinson's disease or Alzheimer's disease.

31. The method of claim 20, wherein the neurologic agent is transported to the olfactory system of the brain of the mammal in an amount effective for treating or preventing a loss of smell.

32. The method of claim 20, wherein the neurologic agent comprises fibroblast growth factor.

33. The method of claim 32, wherein the neurologic agent comprises basic fibroblast growth factor.

34. The method of claim 20, wherein the neurologic agent comprises insulin-like growth factor.

35. The method of claim 34, wherein the neurologic agent comprises insulin-like growth factor-1.

36. The method of claim 20, wherein the neurologic agent comprises insulin.

37. The method of claim 20, comprising applying the pharmaceutical composition to an upper third of the nasal cavity.

38. The method of claim 37, comprising applying the pharmaceutical composition to an olfactory area in the upper third of the nasal cavity.

39. The method of claim 20, comprising applying the pharmaceutical composition to a roof of a nose.

40. The method of claim 20, wherein the pharmaceutical composition comprises a pharmaceutically-acceptable carrier, a lipophilic micelle, a liposome, or a combination thereof.

41. The method of claim 40, wherein the lipophilic micelle or liposome comprises a ganglioside, a phosphatidylcholine, a phosphatidylserine, or a combination thereof.

* * * * *

UNITED STATES PATENT AND TRADEMARK OFFICE
CERTIFICATE OF CORRECTION

PATENT NO. : 6,180,603 B1
DATED : January 30, 2001
INVENTOR(S) : Frey, II

It is certified that error appears in the above-identified patent and that said Letters Patent is hereby corrected as shown below:

<u>Title page,</u>
Item [63], Related U.S. Application Data, should read -- Continuation of U.S. Application No. 08/361,877, filed on Dec. 22, 1994, now U.S. Pat. No. 5,624,898, which is a continuation of U.S. Application No. 08/161,337, filed Dec. 2, 1993, now abandoned, which is a file wrapper continuation of prior U.S. Application No. 07/879,556, filed May 4, 1992, now abandoned, which is a file wrapper continuation of prior U.S. Application No. 07/446,308, filed Dec. 5, 1989, now abandoned, which applications are incorporated herein by reference. --

Item [56], References Cited,
U.S. PATENT DOCUMENTS, insert the following:

| | | | |
|---|---|---|---|
| -- | 4,376,110 | 3/1983 | David et al. |
| | 4,507,391 | 3/1985 | Pukel et al. |
| | 4,584,278 | 4/1986 | Knauf |
| | 4,675,287 | 6/1987 | Reisfeld et al. |
| | 4,666, 829 | 5/1987 | Glenner et al. -- | and
OTHER PUBLICATIONS, insert the following: -- Baker et al., *Exp Brain Res*, 63:461-473 (1986).; Boissière et al., *Decrease of TrkA Messenger RNA Content in Cholinergic Neurons of the Striatum and Basal Forebrain in Alzheimer's Disease*, P03.041 (date unknown), 1 pg.; Bowen et al., *The Lancet*, Jan. 6, 1979, pp. 11-14.; Chia et al., *Biochimica et Biophysica Acta*, 775:308-312, (1984).; Clements et al., *Ganglioside Alterations in Alzheimer's Disease and Treatment of Alzheimer's Disease with GM-1*, AHAF Alzheimer's Disease Research Conference, Feb. 17, 1989 (Abstract), 1 pg.; Cummings et al., *Dementia of the Alzheimer Type*, JAGS, 34:12-19 (1986).; Fischer et al., *Nature*, 329:65-68 (Sept. 3, 1987).; Fredman et al., *Monoclonal Antibody A2B5 Reacts with Many Gangliosides in Neuronal Tissue*, Archives of Biochemistry and Biophysics, Vol. 233, No. 2, pp. 661-666 (1984).; Frey II et al., *Alzheimer's Neurofibrillary Tangles are Labeled by Ganglioside Monoclonal Antibody A2B5*, Alzheimer's Disease: Advance in Basic Research and Therapies, pp. 411-415 (1987).; Hahn et al., *A Public Idiotypic Determinant is Present on Spontaneous Cationic IgG Antibodies to DNA from Mice of Unrelated Lupus-Prone Strains*, Chemical Abstracts Vol. 102 (1985), Abst. No. 102:22541d; Harris, A., *Delivery Systems for Peptide Drugs*, Davis et al., Eds., Plenum Press, NY and London, pp. 191 and 194 (date illegible).; Hussain et al., *Nasal Administration of a Cognition Enhancer Provides Improved Bioavailability but not Enhanced Brain Delivery*, Journal of Pharmaceutical Sciences, Vol. 79, No. 9, pp. 771-772 (Sept. 1990).; Katzman, R., *The New England Journal of Medicine*, pp. 964-973 (Apr. 10, 1986).; Pardridge et al., *High Molecular Weight Alzheimer's Disease Amyloid Peptide Immunoreactivity in Human Serum and CSF Is an Immunoglobulin G*, Abstract from Biochem. Biophys. Res. Commun., 1 pg. (1987).; Smith et al., *Intrandsally Administered Alpha/Beta Interferon Prevents Extension of Mouse Hepatitis Virus, Strain JHM, into the Brains of BALB/cByJ Mice*, Antiviral Reasearch, Vol. 8, No. 5, 6 pp. 239-245 (December 1987).; Wesbey et al., *Physiological Chemistry & Physics & Medical NMR*, 16(2):145-55 (1984)(Abstract-1 pg.). --

UNITED STATES PATENT AND TRADEMARK OFFICE
CERTIFICATE OF CORRECTION

PATENT NO. : 6,180,603 B1
DATED : January 30, 2001
INVENTOR(S) : Frey, II

It is certified that error appears in the above-identified patent and that said Letters Patent is hereby corrected as shown below:

Column 9,
Line 23, after "or" insert -- a --.
Cancel claims "9-13".
Claims "14-20" should be renumbered consecutively -- 9-15 --;
Lines 50 and 52, for the claim reference "15", each occurance should read -- 10 --.

Column 10,
Claims "21-31" should be renumbered consecutively -- 16-26 --;
Lines 7, 10, 18, 36, 50, 56 and 58, for the claim reference "20", each occurance should read -- 15 --;
Lines 13 and 15, for the claim reference "22", each occurance should read -- 17 --;
Lines 22, 25 and 28, for the claim reference "25", each occurance should read -- 20 --;
Lines 32 and 34, for the claim reference "28", each occurance should read -- 23 --.
Cancel claims "32-36".
Claims "37-41" should be renumbered consecutively -- 27-31 --;
Line 53, claim reference "37" should read -- 27 --;
Line 62, claim reference "40" should read -- 30 --.

Signed and Sealed this

Fourth Day of June, 2002

Attest:

JAMES E. ROGAN
Attesting Officer
Director of the United States Patent and Trademark Office